Figure 1:
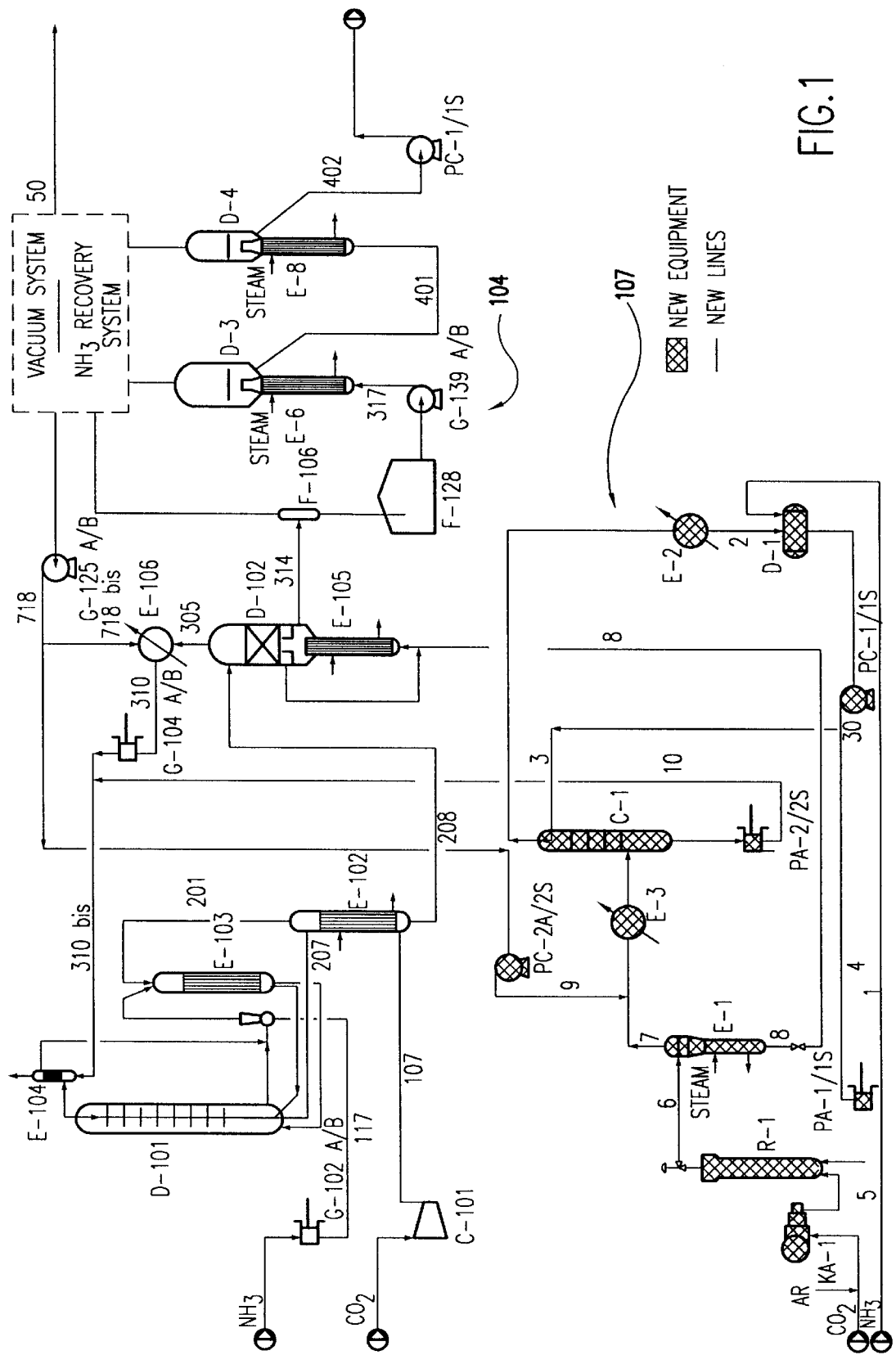

United States Patent [19]

Pagani et al.

[11] Patent Number: 6,150,555
[45] Date of Patent: Nov. 21, 2000

[54] PROCESS FOR UREA PRODUCTION

[75] Inventors: Giorgio Pagani, Milan, Italy; Umberto Zardi, Breganzona, Switzerland

[73] Assignee: Urea Casale, S.A., Lugano-Besso, Switzerland

[21] Appl. No.: 08/405,912

[22] Filed: Mar. 16, 1995

Related U.S. Application Data

[63] Continuation-in-part of application No. 08/059,241, May 7, 1993, abandoned.

[30] Foreign Application Priority Data

Aug. 5, 1992 [CH] Switzerland .............................. 1477/92

[51] Int. Cl.[7] .................................................. C07C 273/04
[52] U.S. Cl. .................................. 564/67; 564/70; 564/72
[58] Field of Search .................................. 564/67, 70, 72

[56] References Cited

U.S. PATENT DOCUMENTS 4,504,679  3/1985  Inou et al. ................................. 564/67
4,613,696  9/1986  Zardi ........................................ 564/67

FOREIGN PATENT DOCUMENTS 479103  4/1992  European Pat. Off. ................. 564/67

*Primary Examiner*—Shailendra Kumar
*Attorney, Agent, or Firm*—Ostrolenk, Faber, Gerb & Soffen, LLP

[57] ABSTRACT

An improved process for urea production as well as a method of retrofitting a pre-existing urea plant based on the Stamicarbon process are disclosed. According to the invention, a high yield reaction space fed by highly pure reagents (NH3 and CO2) and a separating section of the solution leaving the high yield reaction space are added to the pre-existing urea plant, means being provided for recirculating ammonia and carbammate solutions obtained in the separating section to the added high yield reaction space and to the pre-existing reactor respectively.

8 Claims, 1 Drawing Sheet

PROCESS FOR UREA PRODUCTION

This is a continuation-in-part of application Ser. No. 08/059,241, filed on May 7, 1993, now abandoned.

DESCRIPTION

BACKGROUND OF THE INVENTION

The present invention relates to an improved process for urea production, as well as to a method for retrofitting pre-existing urea production plants in which a reaction mixture leaving an urea synthesis reactor is submitted to a stripping step with carbon dioxide (Stamicarbon process).

The invention also relates to a plant for implementing the above mentioned process.

As is well known, the need often arise of increasing the urea production capacity of a pre-existing plant.

To this end, various methods of enhancing the production capacity have been proposed heretofore, such as that described in European Patent application EP-A-0 479 103 by the same applicant.

EP-A-0 479 103 discloses a process wherein highly pure ammonia and carbon dioxide are reacted in a first reaction space, the reaction mixture thus obtained is fed to a recovery section and a synthesis reaction between less pure reagents, substantially recycled by the recovery section (recovery mixture), is carried out.

The need of increasing the urea production capacity as well as of reducing energy consumption is particularly felt in the case of existing plants according to the Stamicarbon Process (STC), including a $CO_2$ stripping section.

The Stamicarbon Process is described in an article by Zardi in "Nitrogen", No. 135, pp. 28–29 (1982). The Stamicarbon Process is described in an article by Zardi in "Nitrogen", No. 135, pp. 28–29 (1982), in an article by Kaasenbrood et al in "Proceedings No. 166, The Fertilizer Society", London (1977), and in an article in European Chemical News Urea Supplement, Jan. 19, 1969, pp. 17, 19 and 20. It employs an ammonia/carbon dioxide mole ratio in the reactor of 2.8 as the optimum ratio.

These kind of plants, widely used for urea production, afford on the one hand a very simple plant layout, but on the other hand have a very limited operating flexibility that render their retrofitting very difficult in terms of capacity increase and energy consumption reductions.

For instance, it is well known that capacity increases over the 10–20% range are difficult to obtain and anyhow, the elevated cost of the investment would make it economically unfeasible.

The aim of this invention is therefore that of providing an improved process for urea production allowing to encrease the capacity and reduce the energy consumption of $CO_2$ stripping plants, for instance of the STC type, at low cost and with minimum modifications of the plant layout.

SUMMARY OF THE INVENTION

This aim is accomplished, according to the invention, by a process of producing urea comprising the steps of:
  reacting ammonia and carbon dioxide in a first reaction space at high temperature and pressure where the ammonia/carbon dioxide ratio is less than 3;
  effecting a gas stripping with said-carbon dioxide of a first reaction mixture leaving said first reaction space;
  feeding the stripped first reaction mixture to a first urea recovery section;
  feeding high purity ammonia and carbon dioxide to a second reaction space;
  feeding a second reaction mixture including urea, carbamate and unreacted ammonia leaving said second reaction space, to a second recovery section,
  separating urea, carbamate and unreacted ammonia in said second recovery section;
  recycling the carbamate and unreacted ammonia leaving said second recovery section respectively to said first and second reaction spaces.

In effect, it has now been found after intensive studies and research, that it is surprisingly possible to enhance production capacity and retrofit in a simple and safe way, $CO_2$ stripping plants for the production of urea according to the modalities described hereinbelow.

According to the present invention, urea synthesis in the first reaction space may be carried out at process conditions currently used in STC plants, such as-for example—at pressures of from 130 to 200 bar and temperatures of from 180 to 200° C.

The carbammate condensing step, the $CO_2$-stripping step of the reaction mixture leaving said reaction space and the urea recovery step in said first recovery section, may also be carried out according to the known process conditions used in a STC plant.

Preferably, the urea synthesis in the second reaction space is carried out in a high-yield "once through" reactor, at pressures of from 250 to 450 bar and at temperatures of from 200 to 230° C.

According to another aspect of the invention, the urea solution obtained from the second high-yield reaction space is then treated in a second recovery section at pressures from 10 to 30 bar or better from 16 to 22 bar, most preferably at 18 bar, comprising at least one distillation column for said solution and a rectification column with relevant condenser for separating high grade ammonia.

The products obtained in this way are:
  an urea solution concentrated up to 74% urea, to be sent to a low pressure section of the first urea recovery section of the plant;
  highly pure $NH_3$ to be recycled to the "once through" reactor before the addition of the $NH_3$ feed;
  a carbamate solution (containing 20% of the $CO_2$ fed to the "once through" reactor) to be recycled to the first reaction space.

According to the present invention, when a capacity increase of over 20% of a pre-existing plant is required, it is advantageously possible to apply the concept of High Efficiency Parallel Reactor in order to accomplish the desired capacity increase and to reduce the energy consumption.

The application of such concept to a pre-existing plant for urea production including:
  a first urea synthesis reactor;
  means for feeding high purity ammonia to a carbamate condenser;
  means for feeding carbon dioxide to a stripper supplied with a first reaction mixture leaving said first reactor;
  a first urea recovery section for separating urea from an aqueous solution of unreacted products leaving the first reactor,
  is carried out, in accordance with the invention, by a method of retrofitting comprising the steps of:
    a) providing a second urea synthesis reactor connected with with means for feeding high purity ammonia and carbon dioxide;

b) providing a second recovery section including at least a distillation and a rectification column downstream of said second urea synthesis reactor;
c) connecting top and bottom of said rectification column with the second urea synthesis reactor and the first urea synthesis reactor respectively;
) providing means for recycling unreacted ammonia and a carbamate solution leaving top and bottom of said rectification column to said second and first urea synthesis reactors respectively.

More particularly, a large part of the requested capacity increase (80%) is obtained in an additional high yield reactor (80%) of the "once through" type without recycle.

Most preferably, said reactor is of the so-called "Vulcan" type.

SHORT DESCRIPTION OF THE DRAWINGS

The appended drawing figure diagrammatically illustrates an embodiment of the present process and apparatus.

As an example, a retrofitting allowing a 50% capacity increase of a plant with $CO_2$ stripping at 1000 MTD urea, the following distribution will be obtained:

capacity of a new "once through" reactor (yield 80%): 400 MTD urea;
capacity of equivalent carbamate solution produced in. the new "once through" reactor as above: 100 MTD;
new capacity of the existing converter: 1000+100=1100 MTD;
total new capacity: 1500 MTD.

The existing line will then be overloaded in the high pressure section HP by only 10%, an overload which may be afforded without particular problems.

Only the low pressure section LP and vacuum section shall require a higher capacity increase, which is neither technically difficult nor excessively expensive.

Since the conversion yield of the existing STC converter is equal to 57% (design) and the conversion yield of the added High Efficiency Parallel Reactor shall be 80% according to the invention, the average conversion yield of the modified plant shall be:

$$\frac{0.57 \times 1100 + 0.8 \times 400}{1500} \times 100 = 63\%$$

with a 6% increase of the overall conversion with respect to the pre-existing plant.

Such increased conversion is also advantageously accomplished with a minor steam consumption of at least 150 kg of steam/T of urea produced in the new operating conditions.

Other aspects and advantages of the invention will be better apparent from the following description of at preferred, though non-limitative, embodiment of a plant according to the invention shown in the attached drawing.

The aforementioned plant comprises a urea synthesis reactor D-101 to which pure ammonia ($NH_3$) and carbon dioxide ($CO_2$) are fed by conventional compressor means C-102 and C-101.

More particularly, ammonia is first fed to a carbamate condenser E-103 by conduit means 117, while carbon dioxide is fed to a stripper E-102 by conduit means 107 and then to the carbamate condenser E-103 by conduit means 201 before entering the urea synthesis reactor D-101.

The stripper E-102 is also fed by the reaction mixture leaving the urea synthesis reactor D-101 through conduit 207.

With 104 is indicated a conventional urea recovery section, comprising a distiller E-105 with relevant separator D-102, two vacuum evaporators E-5 and E-6 with relevant separators D-3 and D-4, as well as a vacuum concentration section 50 of ammonia.

The features of the urea recovery section 104 are per se conventional and well known in the art and will not be further described in detail.

According to the invention, a high efficiency reactor R-1 and a recovery section 107 for separating urea, carbammate and unreacted ammonia leaving reactor R-1, are disposed in parallel to the urea synthesis reactor D-101.

The reactor R-1 is fed by highly pure carbon dioxide by means of compressor means KA-1 and highly pure ammonia by a series of pump means as will be further described hereinbelow.

Advantageously, the reactor R-1 is of the "once-through" high yield type and, most preferably, of the "Vulcan" type.

The recovery section 107 preferably comprises at least a distillation column E-1 of the solution leaving reactor R-1, and a rectification column C-1 in series.

The latter is fed with the top product coming from E-1 along line 7 and yields highly pure ammonia from top and a carbammate solution from bottom.

According to an aspect of the present invention, pure ammonia obtained from rectification column C-1 is recirculated to R-1, before condensating it in E-2, by conduit 2 and 4 and with the help of pump means PC-1/1S and PA-1/1S.

Between the pump means PC-1/1S and PA-1/1S, reflux ammonia is withdrawn at point 30 and sent, along line 3, to the top of column C-1.

According to yet another aspect of the present invention, the carbammate solution leaving the bottom of column C-1 is recycled to the pre-existing converter D-101 by means of pump PA-2/2S and line 10.

Advantageously, an aqueous diluted solution containing $NH_3$ and $CO_2$ obtained in the vacuum concentration section 50 may be recycled to the rectification column C-1 by pump means PC-2A/2S and through conduit 9.

From the bottom of distillation column E-1 an urea solution is also obtained, which is forwarded through conduit 8 to distiller E-105 of the urea recovery section 104.

What is claimed is:

1. A continuous process of producing urea comprising the steps of:
   reacting ammonia and carbon dioxide in a first reaction space at high temperature and pressure, the ammonia/carbon dioxide ratio being less than 3;
   effecting a gas stripping with said carbon dioxide of a first reaction mixture leaving said first reaction space;
   feeding the stripped first reaction mixture to a first urea recovery section;
   feeding high purity ammonia and carbon dioxide to a second reaction space;
   feeding a second reaction mixture including urea, carbamate and unreacted ammonia leaving said second reaction space, to a second recovery section;
   separating urea, carbamate and unreacted ammonia in said second recovery section;
   recycling the carbamate and unreacted ammonia leaving said second recovery section respectively to said first and second reaction spaces.

2. A process according to claim 1, comprising the additional step of recycling urea leaving said second recovery section to said first urea recovery section.

3. A process according to claim 1, wherein said second reaction mixture is separated in said second recovery section by means of at least one distillation and one rectification columns.

4. A process according to claim 3, wherein said separation step of urea, carbamate and unreacted ammonia is carried out at a pressure of from 10 to 30 atm.

5. A process according to claim 3, wherein urea is separated in said at least one distillation column.

6. A process according to claim 3, wherein the carbamate and unreacted ammonia are separated from one another in said rectification column.

7. A process according to claim 3, further comprising the step of feeding to said rectification column an aqueous solution including ammonia and carbon dioxide obtained in a vacuum concentration section of said first urea recovery section.

8. A process according to claim 1, wherein urea synthesis in the second reaction space is carried out at pressures of from 250 to 450 bar and at temperatures of from 200 to 230° C.

* * * * *